United States Patent [19]

Tseng et al.

[11] Patent Number: 5,342,964
[45] Date of Patent: Aug. 30, 1994

[54] PROCESS FOR OBTAINING THE ISOMERIC COMPOUND 1-VINYL-3(E)-ETHYLIDENE PYRROLIDONE

[75] Inventors: Susan Y. Tseng, Staten Island, N.Y.; Philip F. Wolf, Bridgewater, N.J.

[73] Assignee: ISP Investments Inc., Wilmington, Del.

[21] Appl. No.: 40,805

[22] Filed: Mar. 31, 1993

[51] Int. Cl.$^5$ .............. C07D 207/267; C07D 207/263
[52] U.S. Cl. ........................................ 548/552; 548/543
[58] Field of Search ........................ 546/543; 548/552

[56] References Cited

U.S. PATENT DOCUMENTS 5,286,876  2/1994  Tseng et al. .................. 548/552

Primary Examiner—David B. Springer
Attorney, Agent, or Firm—Walter Katz; Marilyn J. Maue; Joshua J. Ward

[57] ABSTRACT

What is provided herein is a process for obtaining the isomeric compound 1-vinyl-3(E)-ethylidene pyrrolidone in a purity of at least 95%, in the form of white, needle-shaped crystals having a melting point of 59°–61° C.

7 Claims, No Drawings

PROCESS FOR OBTAINING THE ISOMERIC COMPOUND 1-VINYL-3(E)-ETHYLIDENE PYRROLIDONE

BACKGROUND OF THE INVENTION

1. Field of the Invention

This invention relates to vinylpyrrolidones, and, more particularly, to 1-vinyl-3(E)-ethylidene pyrrolidone (EVP), and to a method for obtaining this isomeric compound.

2. Description of the Prior Art

Crosslinked polyvinylpyrrolidone (PVP) is made by popcorn or proliferous polymerization of vinylpyrrolidone (VP), in the absence or presence of crosslinking agents, as described in U.S. Pat. Nos. 3,277,066; 3,306,886; 3,759,880; 3,933,766; and 3,992,562; and in an article by F. Haaf et al. in Polymer J. 17 (1), p. 143–152 (1985), entitled, "Polymers of N-Vinylpyrrolidone: Synthesis, Characterization and Uses". Polymerization of vinylpyrrolidone can occur in the absence of added crosslinker because the requisite crosslinker in the process is formed in situ during the first stage heating of vinylpyrrolidone in aqueous caustic solutions at temperatures $>100°$ C., e.g. at 140° C. Such bifunctional monomers, identified as 1-vinyl-3-ethylidene pyrrolidone and ethylidene-bis-3-(N-vinylpyrrolidone), are observed by gas chromatography and other analytical techniques to be present in small amounts in reaction mixtures which had been cooled to room temperature. However, after the polymerization was completed, these bifunctional compounds, could not be found in the final product. Accordingly, the named bifunctional monomers are present only in small amounts as intermediates during the polymerization and are consumed in the process of forming the crosslinked PVP polymer.

Accordingly, an object of this invention is to provide a process for obtaining the isomeric compound 1-vinyl-3(E)-ethylidene-pyrrolidone in a purity of at least 95%.

These and other objects and features of the invention will be made apparent from the following description of the invention.

SUMMARY OF THE INVENTION

What is provided herein is a process for obtaining the isomeric compound 1-vinyl-3(E)-ethylidene pyrrolidone (EVP) having the formula:

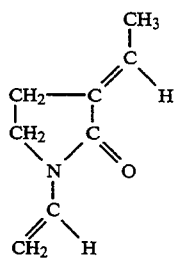

in a purity of at least 95%, in the form of white, needle-shaped crystals having a melting point of 59°–61° C.

This isomeric compound exists in the (E) form, which is defined as the isomer in which the methyl group of the ethylidene radical is positioned away from the oxygen atom of the pyrrolidone ring.

The desired isomeric compound is obtained herein in high yield by reaction of vinylpyrrolidone in aqueous strongly basic solution, in a 2-phase aqueousorganic system, at an elevated temperature, under vigorous agitation. The isomeric compound is recovered from the reaction product by direct fractional distillation of the organic layer of the reaction product.

DETAILED DESCRIPTION OF THE INVENTION

In accordance with the present invention, the desired isomeric EVP compound is produced in a 2-phase reaction mixture comprising an organic phase of vinylpyrrolidone monomer present in an amount of about 25–90%, preferably 40–75%, and, most preferably, about 60%, by weight of the reaction mixture, and an aqueous phase which is a strongly basic solution, such as caustic (NaOH or KOH), or a tetraalkyl ammonium hydroxide solution, suitably with a base concentration of about 2–50%, preferably about 5–10%, by weight of the reaction mixture. The reaction mixture is heated to a reaction temperature of about 120°–170° C., preferably 130°–140° C., in a closed system, under an inert atmosphere, at ordinary or higher initial pressures, suitably at an initial pressure of 0–3 bars of an inert gas, such as nitrogen. The reaction to convert VP monomer to isomeric EVP compound is carried out for about 0.5–10 hours, preferably 1–3 hours, at, e.g. 140° C., while the reaction mixture is subjected to vigorous agitation, e.g. about 800 rpm.

At the conclusion of the reaction, 2 layers are obtained as the reaction product. The top layer is an organic layer which contains about 50–80% by weight of unreacted VP and about 5–30% of the desired isomeric EVP compound, and, more particularly, about 70–75% VP and 15–20% EVP. The bottom layer is an aqueous caustic layer which also contain small amounts of VP and EVP.

The isomeric compound then is isolated from the reaction product by direct fractional distillation of the organic (top) layer.

In this direct distillation method of recovery of the isomeric compound from the reaction mixture, the organic phase, which is the top layer, is separated from the aqueous solution, which is the bottom layer, and then the organic layer is flash distilled under vacuum. A suitable vacuum distillation apparatus includes a receiving condenser connected to the distilling head at one end and to a receiving flask at the other end. The first cut contains unreacted VP and 2-pyrrolidone by-products which are distilled out from the organic layer as a clear liquid at 50°–75° C. at 1 mm Hg. The remaining isomeric compound then is distilled out at a higher pot temperature of about 80°–90° C. and obtained as a colorless solid which crystallizes on the walls of the receiving condenser. This solid can be collected from the walls, or, preferably, the walls are heated to melt the solid to a liquid, and the liquid is recovered and solidified. Upon recrystallization of the solid product from water and drying, the desired isomeric (E) compound is obtained as white, needle-shaped crystals having a melting point of 59°–61° C. The (E) isomeric chemical structure is confirmed by gas chromatographic, mass spectroscopy and $^1H$ and $^{13}C$ NMR analysis.

The process of rapid and efficient production of EVP in large quantities herein is based on the following two interdependent parameters.

(1) An initial high concentration of caustic catalyst in the reaction mixture, and (2) Maintenance of a two-phase organic/aqueous system in the reaction mixture throughout the course of the reaction.

Considering parameter (1), the use of a high (2–50%) caustic concentration has a dual effect. First, the high concentration of a strong inorganic hydroxide causes the aqueous layer to maintain its integrity and "salt out" the organic compounds, most notably, vinylpyrrolidone. Such is not the case in conventional PVP syntheses using a low concentration of caustic solution in which the aqueous and organic phases merge. Secondly, the high caustic concentration in the process of this invention accelerates the reaction of VP to EVP. Indeed, the caustic, which is a catalyst for the formation of EVP from VP, is consumed through reaction with 2-pyrrolidone, a by-product of the reaction. The 2-pyrrolidone, in turn, is readily hydrolyzed by base to sodium 4-aminobutyrate (4-AB), which is not a catalyst for EVP formation. However, (4-AB), being water soluble, can serve as the salt necessary to maintain the 2-phase system in the process.

Transfer of the vinyl moiety of the VP monomer which is necessary for EVP synthesis appears to take place at or near the organic-water interface of the 2-phase reaction system. Once the VP transfer is complete, the slightly acidic 2-pyrrolidone by-product drifts into the basic aqueous phase and EVP moves to the organic medium. In fact, both the strong base and other salts are present overwhelmingly in the aqueous layer during the process. The conversion of 2-pyrrolidone to 4-AB in the presence of aqueous base reduces the concentration of base in the organic phase, thereby avoiding an undesired further reaction of EVP to ethylidene-bis-vinyl-pyrrolidone (EVBP).

The yield of isomeric EVP obtained in the process of the invention is about 5–30% based on reacted VP.

The invention will now be illustrated with reference to the following examples.

EXAMPLE 1

400 g of a reaction mixture of 60% VP, 10% NaOH and 30% water was heated at 135° C. for 1.5 hours under 0.2 bar of nitrogen pressure (<20 ppm $O_2$). The organic reaction product (top layer) then was separated from the aqueous reaction product (bottom layer). The organic layer weighed 200 g and contained 61% VP and about 17% of the isomeric (E) compound based on the total weight of the layer.

The organic layer then was flash distilled at 60°–75° C. under 1 mm Hg. A mixture of VP and 2-pyrrolidone was collected in the receiving flask. Upon further distillation at 80°–90° C. under 1 mm Hg, the isomeric compound distilled out as a vapor and solidified on the walls of the condenser. The walls then were heated to 70° C. and the isomeric compound melted and was collected as a liquid in the receiving flask. After cooling to a solid, the isomeric compound was recrystallized from an ice water bath. The yield of isomeric EVP obtained was 30 g or 25%, as calculated below:

$$\%EVP \text{ Yield} = \frac{EVP \text{ Crystals (30 g)}}{\text{Wt. of the Initial } VP \text{ (240 g)} - \text{Wt. of Unreacted } VP \text{ (120 g)}} \times 100$$

EXAMPLES 2–3

A stainless steel Buchi reactor was used as the reaction vessel at an initial pressure of 3 bars of nitrogen pressure and at room temperature. The reaction was carried out at 140° C. for 2 hours using 320 g of VP, 40 g of 50% NaOH solution and 40 g of distilled water (Ex. 2), and 320 g of VP and 80 g of 50% NaOH solution (Ex. 3). The organic reaction product (top layer) was separated from the aqueous reaction phase, and distilled directly under 1 mm Hg to provide yields of 25%, and 28%, respectively, of the isomeric compound.

EXAMPLE 4

A stainless steel Buchi reactor was used as the reaction vessel at an initial pressure of 3 bar of nitrogen pressure at room temperature. The reaction was carried out at 135° C. for 1.5 hours using a reaction mixture of 320 g of VP and 80 g of 50% of an aqueous NaOH solution. The organic reaction product (top layer) was separated from the aqueous phase and distilled directly under vacuum. A yield of 30% of the isomeric compound was obtained.

The isomeric EVP compound of the invention finds utility as a crosslinking agent in the direct polymerization of vinylpyrrolidone to crosslinked polyvinylpyrrolidone at low temperatures.

While the invention has been described with particular reference to certain embodiments thereof, it will be understood that changes and modifications may be made which are within the skill of the art. Accordingly, it is intended to be bound only by the following claims, in which:

What is claimed is:

1. A process for obtaining the isomeric compound 1-vinyl-3(E)-ethylidene pyrrolidone comprising
    (a) providing a 2-phase reaction mixture comprising an organic phase and an aqueous phase, wherein the organic phase is vinylpyrrolidone in an amount of about 25–90% by weight of the reaction mixture, and an aqueous phase which is an aqueous solution containing 2–50 wt. % of a strong base selected from sodium hydroxide, potassium hydroxide and a tetraalkyl ammonium hydroxide, under vigorous agitation, in an inert atmosphere,
    (b) heating said reaction mixture at about 120°–170° C. for about 0.5–10 hours to provide a reaction product comprising a top layer which is an organic layer which is predominately vinylpyrrolidone with a lesser amount of said isomeric compound and a bottom layer which is an aqueous layer,
    (c) separating the organic layer from the aqueous layer,
    (d) fractionally distilling the organic layer under vacuum, and
    (e) isolating the desired isomeric compound.

2. A process according to claim 1 wherein, in (d), vinylpyrrolidone and 2-pyrrolidone are first distilled out at 50°–70° C. at 1 mm Hg.

3. A process according to claim 1 wherein, in (e), the isomeric compound is obtained as a colorless solid upon further distillation at about 80°–90° C. at 1 mm Hg.

4. A process according to claim 1 wherein the yield of the isomeric compound is about 5–30% based on reacted vinylpyrrolidone.

5. A process according to claim 3 wherein the solid obtained is heated to form a liquid of the isomeric compound which is collected.

6. A process according to claim 1 wherein the organic phase contains 40–75% vinylpyrrolidone and the organic phase contains 5–10% by weight of base.

7. A process according to claim 1 wherein said reaction temperature is about 130°–140° C.

* * * * *